United States Patent [19]

Krumme et al.

[11] Patent Number: 4,550,870

[45] Date of Patent: Nov. 5, 1985

[54] STAPLING DEVICE

[75] Inventors: John F. Krumme, Woodside; Darel E. Hodgson, Palo Alto, both of Calif.

[73] Assignee: Alchemia Ltd. Partnership, Palo Alto, Calif.

[21] Appl. No.: 541,546

[22] Filed: Oct. 13, 1983

[51] Int. Cl.$^4$ ............................................. A61B 17/04
[52] U.S. Cl. ................................. 227/19; 128/334 R; 227/DIG. 1; 227/120; 227/129; 227/156
[58] Field of Search ...................... 128/334 R, 334 C; 227/DIG. 1, 19, 156, 120, 129

[56] References Cited

U.S. PATENT DOCUMENTS

| | | | |
|---|---|---|---|
| 3,940,935 | 3/1976 | Richardson | 60/528 |
| 3,953,253 | 4/1976 | Clark | 148/131 |
| 4,006,747 | 2/1977 | Kronethal et al. | 227/DIG. 1 |
| 4,016,721 | 4/1977 | Richardson et al. | 60/528 |
| 4,109,844 | 3/1978 | Becht | 227/19 X |
| 4,144,057 | 3/1979 | Melton | 75/134 C |
| 4,179,057 | 12/1979 | Becht et al. | 227/19 |
| 4,281,785 | 8/1981 | Brooks | 227/156 X |
| 4,304,613 | 12/1981 | Wang et al. | 148/11.5 N |
| 4,351,466 | 9/1982 | Noiles | 227/19 X |

FOREIGN PATENT DOCUMENTS 2703529 3/1978 Fed. Rep. of Germany .

Primary Examiner—Paul A. Bell
Attorney, Agent, or Firm—Howard L. Rose

[57] ABSTRACT

A stapling device utilizes heat recoverable material (the driver) having shape memory to drive staples through materials to be joined and in one embodiment, against an anvil for crimping the ends of the staples. The heat recoverable material, preferably a metal such as Nitinol, may have heat applied by a heater mounted on at least one surface thereof or by induction or other method of heating. If a heater is mounted on a surface of the driver, upon insertion of the driver into the staple device, the heater makes electrical connection with terminals for connection to a supply circuit. In a specific embodiment staples may be provided, fabricated from heat recoveralbe metal so that each staple may carry its own heat recoverable, staple driving element. The staple tines may have a heat recoverable shape with the ends of the tines directed toward one another so that staple closure occures as heat migrates from the staple driving region to the tines thereof. Alternatively, the heat recoverable staple may complete a circuit through the staple upon contact with the anvil, thus heating the staple. Alternatively, the staples may have a heat recovered state with the ends parallel to one another so that the application of heat will open the staples and permit ready removal.

21 Claims, 19 Drawing Figures

U.S. Patent  Nov. 5, 1985  Sheet 1 of 3  4,550,870
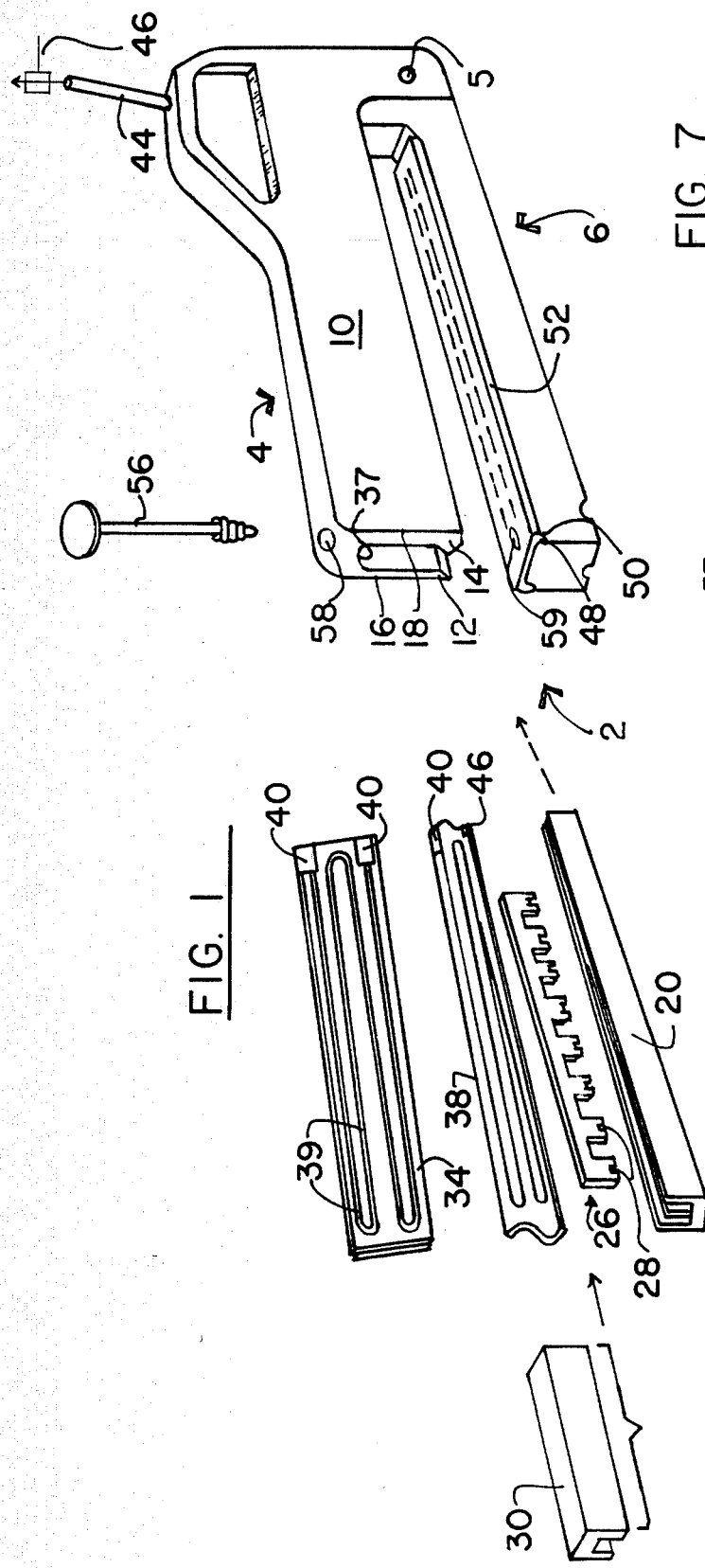
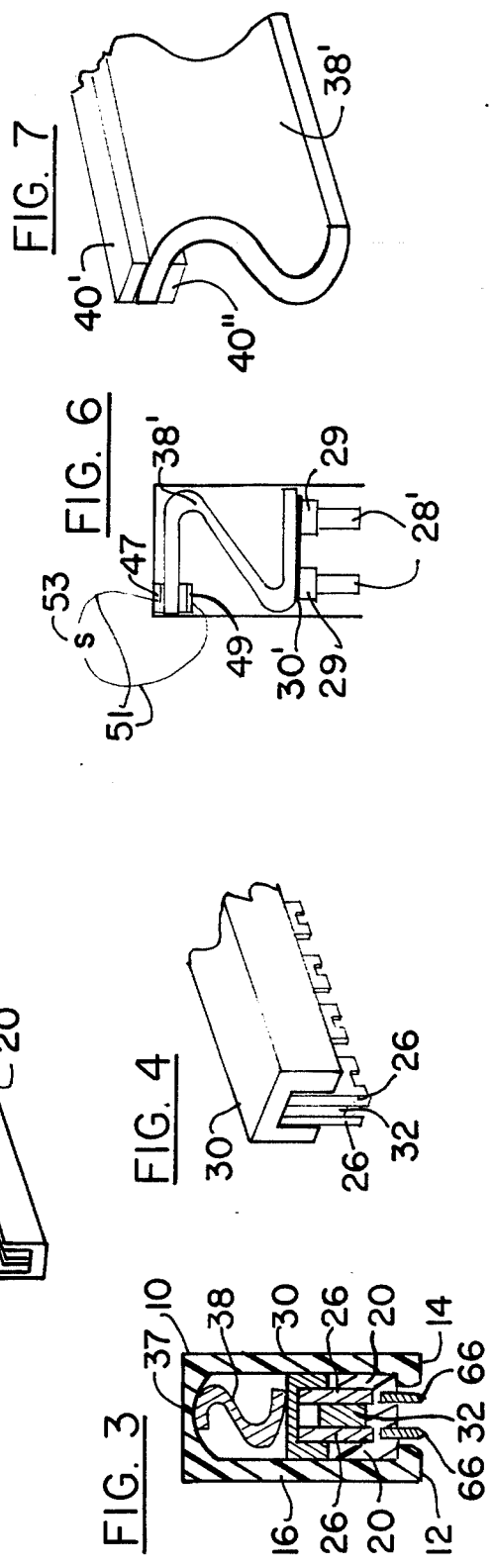

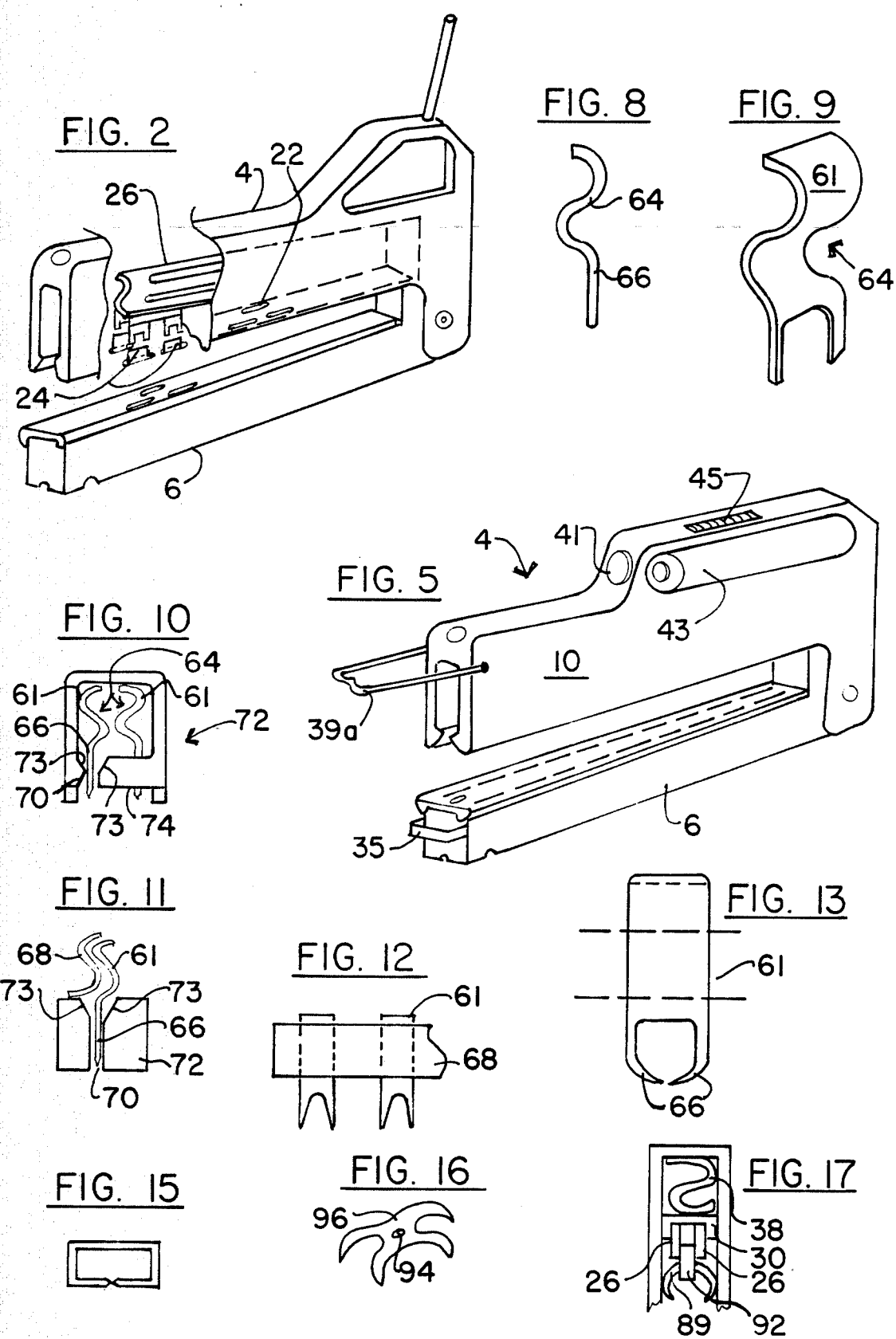

STAPLING DEVICE

RELATED APPLICATION

This application is related to copending application Ser. No. 277,112, filed on June 25, 1981 by John F. Krumme and entitled Shape Memory Surgical Staple Apparatus and Method for Use In Surgical Suturing.

BACKGROUND OF THE INVENTION

The present invention relates to stapling devices and more particularly to surgical stapling devices utilizing a heat recoverable element to drive the staples.

Surgical stapling devices are employed in many surgical procedures in place of conventional suturing procedures; stapling produces less trauma to tissue than suturing. Surgical stapling devices, such as disclosed in U.S. Pat. Nos. 3,252,643; 3,692,224; 4,216,891; etc., conventionally employ a pair of parallel elongated jaws pivoted so that they may be placed on opposite sides of the ends of regions of tissue to be joined. One of the jaws carries the staples and the other jaw carries the anvil against which the staples are pressed and formed after penetrating the tissues to be joined.

In use, the tissues to be joined are placed side by side between the jaws and a knob is turned or other type of mechanical actuating mechanism operated to cause a lead screw or other type of drive to drive one jaw toward the other and clamp the tissues. When the surgeon determines that sufficient clamping force has been developed on the tissues, the knob is caused to engage a bar that in turn engages a staple driving mechanism. The mechanism causes the staples to pierce the tissues and be pressed against the anvil whereby the ends are turned over to retain the staples in the tissue.

The problems with this mechanism relate to the fact that the operation is relatively slow, the force applied to hold the tissues is basically controlled wholly by the surgeon, and thus may result in damage to the tissue. Further, the device is large, cumbersome, and awkward to use particularly in tight locations internally of the body.

Although the invention is described as a surgical stapling device, it is readily apparent that such a device may readily be employed for many different applications, particularly where it is desirable to clamp and then insert numerous staples for purposes of holding, i.e., stapling in one operation the line of material that is clamped between the jaws. Examples of those uses are in construction work applications. The invention is described with respect to surgical uses but as indicated, is applicable to a wide range of applications.

SUMMARY OF THE INVENTION

In accordance with the present invention, a material having a mechanical, i.e., shape, memory is employed to drive the staples thus eliminating the need for the unwieldy and large knob and associated mechanisms and their attendant problems found in present day surgical stapling devices of the dual-jaw type.

The material having a shape memory may be a nickel titanium alloy of the type disclosed in U.S. Pat. No. 3,174,851 known by the name "Nitinol." Further details of these materials may be found in NASA Publication SP 5110 entitled "55-NITINOL - The Alloy with a Memory, Its Physical Metallurgy, Properties, and Applications, C. M. Jackson et al, 1972. Many other materials having similar characteristics are also known. The characteristic of these materials utilized in the present invention is the ability of a heat recoverable metallic material, after stressing to a non-stable configuration, while below a specific transition temperature, to return to its pre-stressed configuration when heated above such temperature.

In the present invention, a pair of parallel jaws of the same general configuration as in the prior art may be clamped together by a coarse, threaded screw, a spring clamp or other suitable quick acting clamp. Thereafter, an electric heater is energized by a battery, or other type of electrical source, to heat the heat recoverable metal which may preferably have an "S" or a "C" cross sectional shape prior to heating. Upon heating, the material, which is located above the base of the generally U-shaped staples, straightens out and drives the staples through the flesh clamped between the jaws and into contact with the anvil. The ends of the staples are turned and stapling is completed.

In one specific embodiment of the invention, a narrow, elongated, preferably plastic member has two rows of parallel staggered slots. A pair of staple driving members, each having a plurality of generally rectangular fingers extending from a long cross member, each has a separate finger located in each of the slots of a different one of the rows. A staple may be located as desired in the end of any slot below a finger thus establishing two rows of staples in staggered relationship.

The plastic member is held in a hollow, generally U-shaped jaw having the heat recoverable "S" or "C" shaped member disposed between the base of the U-shaped member and the top of the fingered members or in the latter instant, a bar extending over the top of the fingered members.

A metallic thin film or serpentine wire heater is formed or disposed on one or both sides of the heat recoverable member and provides sufficient heat to the heat recoverable member to quickly raise its temperature above its transition temperature when the heater is connected across an appropriate power supply. The subsequent recovery of the metal to its straight form upon heating, drives the staples through the tissue and against the anvil, whereby to form the staple ends to hold in the tissue.

In operation, the surgeon places the tissue to be stapled together, between the jaws of the device, clamps the jaws together and throws the switch to the heater. Since clamping may be effected by a quick acting mechanism of a rigid construction, clamping forces are controlled. Further, the quick acting heater produces rapid stapling. The device, due to the elimination of the large knob and related operating mechanisms, is conveniently smaller than the prior art devices. Thus, the devices of the present invention are smaller, less expensive, and faster acting than the prior art devices and require far less attention from the surgeon, resulting in consistently better performance. Significantly, as in the prior art devices, the surgeon can proportionally control staple movement with the present invention as well as the existing units; in the present case by controlling the time of the heating interval. Further, the number of staples to be inserted may be controlled by movement of the driving member longitudinally of the body of the device, each staple having a separate staple drive for activation by the movable elongated driver carrying the heater.

In one alternative form of the device, each staple is made of shape memory metal and has a small S-shaped upper region which when heated, expands and projects the staple through the tissue and against the staple end shaping anvil. To heat the individual staples, a thin strip heater may again be employed. The heater may be provided with a tacky material along one or both sides to hold the staples in a spaced relation corresponding to the spacing between the slots in the staple holder. The strip may also be brought into contact with an adjacent surface such as of the staple holder so that as the "S" or "C" shaped top of the staples expand and extend into the slots, the heater is stripped from the staples. The length of the expanded end of each staple is sufficiently short that it may be left on the staple. If desired, a break line may be provided so that the expanded end of the staple may be snapped off.

In still another embodiment of the last-mentioned staple, the tines may be provided with a memory shape in the closed position. As the shaped upper end of the staple is heated, it expands and drives the staple. Concurrently, the heat applied to the upper end spreads to the tines so that after penetration of the tissue, the tines become heated above their transition temperature and the ends curl and close on one another to complete the stapling operation. Alternatively, the staples, upon passing through the tissue, may complete an electric circuit by contacting a base plate, the current passing through the staples heating them. The force required to be exerted on the tissues in such a case is somewhat less than where stapling is affected by pressing the ends of the staples against an anvil with obvious beneficial results.

In still another embodiment of the invention, the staples may have a heat recoverable memory with the tines in the parallel position. In such case, the staple, once secured, may be readily removed by the application of heat which will cause the staples to recover to their original shape.

The heater-heat recoverable member combination may be formed by plating or coating a conductor on the non-tacky side of a plastic tape, for instance, 3M's Kapton. The conductor (Nickel, Ni-chrome, etc.) high resistivity film is then etched to provide a suitable heater wire, preferably serpentine, and ends pads for contact with terminals formed in the stapling device. The sticky side of the tape in then contacted with the heat recoverable member which has previously been deformed to its desired shape.

The same heater tape may be employed for the staples wherein each has its own heat recoverable member. The staples are arrayed along the tacky side of the tape at intervals corresponding to the intervals between slots in the plastic staple holder previously mentioned.

Heating may also be provided by coating the staples with a thin layer of electromagnetic material and inducing eddy currents therein by a varying magnetic field. Hot air may also be employed, or in construction work, a torch or the like may be employed to provide the necessary heat.

The desirable transition temperature of the heat recoverable metal employed for surgical devices is preferably in the 50° C.-60° C. range (50.0 to 50.2 atomic % Nickel; the rest Titanium) well below the temperature of degradation of the mastic employed on the Kaptan tape. Other heat recoverable materials or Nitinol mixtures may be employed to provide the same or other transition temperatures, beta brass and nickel-titanium alloys being examples of such materials.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein:

FIG. 1 is an exploded view of one form of the apparatus of the present invention.

FIG. 2 is a perspective view of the assembled apparatus of FIG. 1.

FIG. 3 is an end view, in cross section of the assembled apparatus of FIG. 2 illustrating the jaws of the apparatus.

FIG. 4 is a perspective view of the staple driving mechanism.

FIG. 5 is a perspective view of a modification of the housing of the mechanism permitting inclusion of a battery therein.

FIG. 6 is a front view of a modification of the device of FIG. 1.

FIG. 7 is a view in perspective of a part of the apparatus of FIG. 6.

FIG. 8 is a side view of a form of staple.

FIG. 9 is a view in perspective of the staple in FIG. 8.

FIG. 10 is an end view in section of an apparatus capable of utilizing the staple of FIGS. 8 and 9.

FIG. 11 is an end view of the apparatus of FIG. 8 with the heater applied to the staples.

FIG. 12 is a side view in elevation of the staple-heater arrangement of the apparatus of FIG. 11.

FIG. 13 is a front view in elevation of a modified form of the staple in FIGS. 8 and 9.

FIG. 15 is a front view of a staple formed by any one of the above mechanisms.

FIG. 16 is a view in perspective of a four-pronged staple that may be employed with the modified staple gun of FIG. 17.

FIG. 17 is a front view of the internal structure of a staple gun for use with the staple of FIG. 16.

DESCRIPTION OF THE INVENTION

Figure 14:
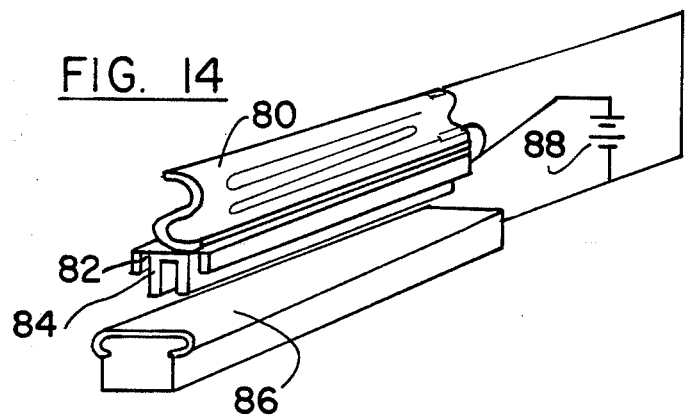
FIG. 14 is a side view of a device in which a circuit is completed through the staple.

Referring specifically to FIGS. 1-4, of the accompanying drawings, a stapler 2 comprises a pair of elongated jaws 4 and 6 joined by a pivot pin 5 to permit pivoted movement of the jaws relative to one another.

Upper jaw 4, as viewed in FIGS. 1-4, comprises a hollow inverted U-shaped member 10 having inwardly directed ridges 12 and 14 extending along the length of the inner surfaces of legs 16 and 18 of the member 10.

A generally rectangular member 20 is adapted to be inserted in the member 10 and forms the staple holder of the apparatus. Specifically, the member 20 is provided with two rows of alternately arranged (staggered) slots 22 extending through the member 20, vertically as viewed in FIGS. 1-3. A staple 24 is located in each slot 22 with the open end of the staple facing the jaw 6. It should be noted that the members 4 and 20 may be made of plastic and may be molded as a single piece.

Multifingered members 26 are provided with fingers 28 of a size and spacing between fingers such that the fingers are received with little play in the slots 22. One member is located in each row of slots 22; the number of fingers on each member being determined by the number of staples it is desired to use for a specific application.

A shallow inverted U-shaped bar 30 is disposed on top of the members 26. A guide 32 is located between the members 26 to maintain alignment of the members during a stapling operation so that when a downward force is applied to the bar 30, the fingers 28 are pushed against the tops of the staples, the guide 32 preventing binding of members 26.

Referring now specifically to FIG. 1, the staple activating mechanism is discussed. A heat recoverable member 34 in its stable form is illustrated at numeral 36. Such member has a generally flat shape defining a thin vertical member as illustrated at numeral 36. Such member has a generally flat height somewhat greater than the distance between base 37 of the U-shaped member 10 and the top of the bar 30 when engaged with the top of the edges of the member 20.

The shape illustrated at numeral 36 is the "memory" shape of the device and this is achieved by forming the member in the shape 36 and then raising its temperature to the extent necessary to impart memory, i.e., about 900° F. for one form of Nitinol. After the member is cooled, it is bent into a desired shape—an "S" as viewed at 38 in FIG. 1. The shape may also be a "C" or any other shape that produces large expansion with large forces. The dimension of the "S" is such that member 38 may be inserted between the base 37 and top of bar 30 as viewed in FIG. 3.

A heater 39, which may be a Mylar film heater, is disposed along one surface of the member 34 terminating in contacts 40. When the heat recoverable strip 34 is inserted into the member 10, the contacts 40 engage corresponding contacts 42 in the back (pivot end) of the jaw 4. Contact with a battery may be made via a cable 44 containing a switch 46.

The lower jaw 6 has slots 48 formed along the outer surfaces of the sides thereof to receive the edge ridges 50 of an anvil 52 placed on the lower jaw 6. The anvil 52 is formed with conventional staple closing depressions 54 each located under a staple containing slot 22 in the jaw 4.

The upper jaw 4 is also provided with a clamping screw 56 which is used to hold the jaws 4 and 6 together during use of the device. Specifically, in use, the tissues to be joined are placed side by side between the jaws 4 and 6 and the screw 56 which extends through hole 58 in member 10 is rotated to thread screw into threaded hole 59 in jaw 6 to draw the jaws 4 and 6 together. The switch 46 is now activated and the element 34 is heated. As the transition temperature of the element 38 is approached, it rapidly attempts to revert to the shape illustrated at 36 in FIG. 1 pushing down with great force on the bar 30, forcing the staples 24 through the tissue and against the anvil where the ends of the staples are turned over to complete the stapling operation.

In another embodiment of the invention, illustrated in FIG. 5, the upper member 4 is provided with a battery compartment 41 in which may be seated a battery 43. A finger-operated slide switch 45 is provided in a convenient location such as the top of the member 4. Upon closing of switch 45, the heater 39 is connected across the battery, heating the member 34 and driving the staples.

In the embodiment of FIG. 5, a quick clamping mechanism is employed. Such mechanism comprises a protrusion 35 extending forward from lower jaw 6 which is adapted to be engaged by a loop 39a of spring wire pivoted to the jaw 4. The loop may be rotated downward to a position under protrusion 35 thus establishing a fixed spacing between jaws 4 and 6 providing the benefits previously indicated.

Referring specifically to FIG. 6 of the accompanying drawing, an alternative mechanism is disclosed for selecting the number of staples to be driven. Individual staple drivers 28' with enlarged head regions 29 are provided. A bar 30' is secured to the bottom of the heater 38' and both are slidable in the body member 10.

The S-shaped member 38' is provided with electrical contacts 40' and 40" (see FIG. 7) on the upper and lower surfaces, respectively, of the upper end of the member. These contacts engage contacts 47 and 49, respectively, disposed in the body 10 and connected via flexible leads 51 to an external source 53. If an internal battery source such as source 43 in FIG. 5 is employed, then external leads are not required.

As a result of such an arrangement, the heater 38' may be adjusted in and out so as to select the number of staples in each row to be inserted.

In an alternative form of the invention, each staple 61 (of FIGS. 8 and 9) includes its own driving mechanism. Referring to FIGS. 8-12, each staple includes an S-shaped region 64 terminating in a straight staple region 66. The staple 61 is made out of a heat recoverable metal so that when heated, the S-shaped regions straighten out and the staples are driven through the tissue and the ends turned over as before.

Heating may be accomplished again by a strip heater 68 of FIGS. 11 and 12, having a sticky surface to which the staples 61 adhere. The staples 61 are inserted into slots 70 in block 72 positioned in inverted U-shaped member 74 of the upper jaw of the device. The slots 70 in the block 72 are tapered as at 73 to accommodate the S-shaped part of 64 of the staple 61 as it is heated and descends downwardly, as viewed in FIGS. 8 and 9, but before it fully straightens out.

When the staples are inserted into slots 70, the sticky surface of the heater 68 extends into contact with the upper surface of the block 72 so that it is peeled off of the staples as they extend more deeply into the slots 70. When the staples are fully extended, the device is opened and the upper jaw pulled up so that the staples are pulled out of the slots 70 and the heater strip 68 is fully disengaged from the staples.

In another alternative form of the staples of FIGS. 8-12, their shape at time of use is the same as in those Figures, but the unstressed shape is as viewed in FIG. 11 with the tines 66 of the staple in the open position. Since the heat is applied initially to the region 64 of ths staple, the region 64 straightens first and drives the staple through the tissue. Thereafter, the heat reaches the region of the tines and they resume the shape illustrated in FIG. 13; thus the closing action of the staples is enhanced.

It should be noted that the specific heat recoverable material employed will depend upon many factors such as desired transition temperatures, mechanical properties and related matters. Heating may be accomplished as indicated by hot air blowers, hot water carrying tubing, and other known or to be developed forms of heat delivering devices. Presently, in addition to the Nitinol memory materials, there are such materials as AuCd, FePt$_3$, Beta brass and InTl. Transition temperatures, particularly of the Nitinol materials, may readily be selected by control of atomic percentage of the materials. Transition temperatures may be made to range from cryogenic temperatures to approximately 150° C.

Referring now specifically to FIG. 14 of the accompanying drawings, there is illustrated an arrangement wherein a driver is employed merely to move the staples until they touch a base member at which time an electric current is passed through the staples to cause them to close. In such an arrangement, no external stapling force is required to clinch the staples. Specifically, a driver is provided for the staples. The driver is illustrated as a Nitinol driver 80, but it may take the form of a prior art driver, i.e., a screw turned by hand as in the prior art.

The driver of whatever form presses down on a bar 82 overlying staple drivers 84. A conductive plate 86 is disposed in about the location of the anvil 52 of FIG. 1. A source 88 of electricity is connected between bar 82 and plate 86 such that when a staple is forced through tissue or other work piece and contacts plate 86, a current path is completed through the staple which becomes heated. A staple of the type illustrated in and described with respect to FIG. 13 is employed. Thus, upon generation of heat, the staple assumes the configuration of FIG. 13, and the stapling operation is complete.

If the driver is of the type discussed with respect to FIG. 1, then the heater may also be connected across the source 88.

Thus far the description has been limited to the in-line stapling devices of one or more rows.

In staples employed in the apparatus of the invention, it is desirable that the staple not rotate in the body. Such rotation would readily result in a number of the staples having their opposed ends lying outside, rather than inside the body, thereby greatly complicating any needed removal procedure. The devices thus far described herein form a staple of the shape illustrated in FIG. 15.

Another form of staple that may be employed is illustrated in FIG. 16 of the accompanying drawings. Such a staple 89 may be driven by a tool much like that of FIG. 1 wherein the four fingers 90 of the staple are each driven by a different member 28 (see FIG. 1). The mechanism for holding the individual staples must be changed and merely comprises a centrally located rod 92, see FIG. 17, for receiving the staple through hole 94, see FIG. 16. Appropriate guide surfaces are provided as necessary.

In such a device, the staple, since it grasps the tissue in dual pincers and has a flat member 96 which cannot penetrate the tissue, cannot rotate and become infected in the tissue.

Figure 18:
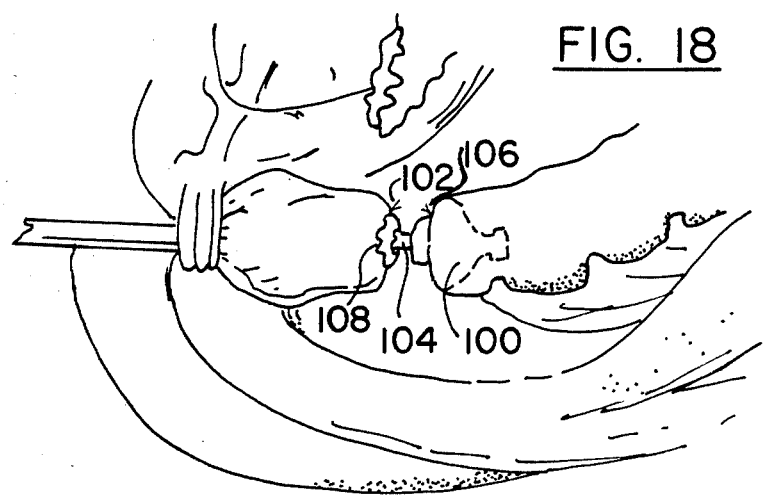
FIG. 18 is a drawing of a partially completed colon resection procedure employing an end-to-end anostomosis instrument.

Referring now specifically to FIG. 18, there is illustrated a portion of a colon this is to be resected and the tool required to perform the anastomosis. In this drawing, the diseased portion of a colon has been removed. The end-to-end anastomosis instrument is introduced into the anus and the anvil 100 is extended beyond the end of the colon adjacent the rectum. Previously applied purse string 102 is drawn tightly about shaft 104 carrying the anvil. The anvil 100 is now inserted into the proximal colon. Purse string 106, previously applied, is now drawn tight about the stem 102.

The shaft 102 is now moved to the left to clamp both tied ends of the colon between anvil 100 and cartridge 108 which carries several rows of staples. The cartridge is now activated to staple the two ends together, a circular knife is activated cutting away the tissue inwardly of the staples whereby the anvil 100 may be maneuvered out of the body.

Figure 19:
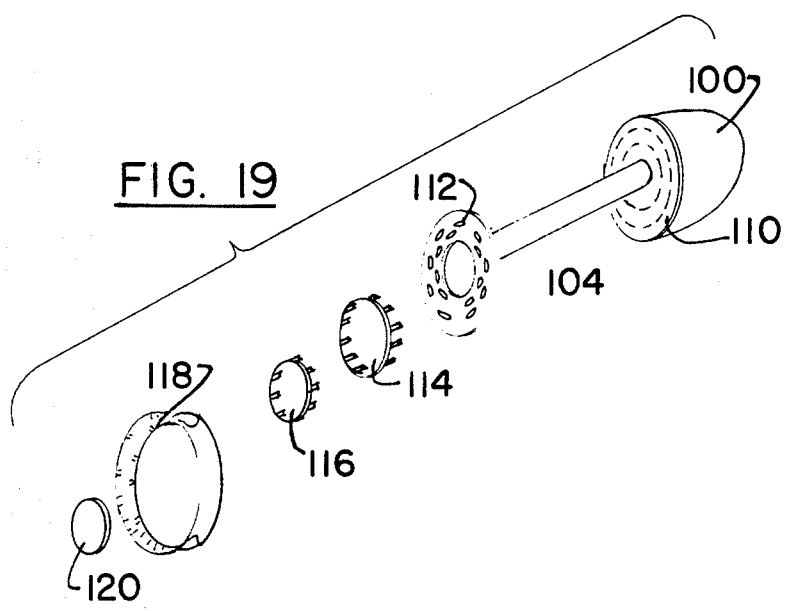
FIG. 19 is a view of such an instrument modified to employ Nitinol drivers and/or staples.

Referring now specifically to FIG. 19 of the accompanying drawings, a modification of the standard device of FIG. 18 for use in the present invention is shown.

The anvil 100 is provided with two concentric rows of the usual staple turning indentations 110. The cartridge comprises a staple holder 112, a circular form of the member 20 of FIG. 3. The holder has two rows of holes aligned along shaft 102 with the indentations 110 of the anvil. The holes receive the staples. Two circular drivers 114 and 116 corresponding to the members 26 of FIG. 1 are provided which contact and are driven by a circular Nitinol element 118 that is C-shaped in cross section. Upon heating of the element 118, the staples are driven as in the device of FIG. 1. A cutter 120 is also provided which may also be driven by a separately excited Nitinol driver.

Although the invention has been described in its preferred forms with a certain degree of particularity it is understood that the present disclosure of the preferred forms has been made only by way of example and that numerous changes in the details of construction and the combination and arrangement of parts may be resorted to without departing from the spirit and the scope of the invention as hereinafter claimed.

What is claimed is:

1. A stapling device including
   a first member having staple receiving means for carrying staples therein,
   means for driving the staples for causing them to pierce material to be stapled,
   said means for driving comprising a driving member deformed into a partially collapsed shape and upon application of heat being recoverable to an expanded shape,
   said means for driving being located in said first member between said staples and an opposing inner surface of said first member and further comprising means for heating said deformed member.

2. A stapling device apparatus comprising:
   a pair of elongated parallel jaws for clamping therebetween material to be stapled,
   one of said jaws having apertures for carrying staples therein and including means for driving the staples for causing them to pierce material clamped between the jaws,
   said means for driving comprising a deformed and at least partially collapsed, member having shape memory and being heat recoverable to an expanded shape,
   said one jaw defining a region for positioning said deformed member in a staple driving relationship upon heating of said heat recoverable member, and means for heating said heat recoverable member.

3. The apparatus according to claim 2, wherein said deformed member has in the deformed state a curved shape and in the recovered state a generally flat shape.

4. The apparatus according to claim 3 where said member is metallic and has in the deformed state the shape of an "S".

5. The apparatus according to claim 3 wherein said member is metallic and has in the deformed state the shape of a "C".

6. The apparatus according to claim 2 wherein said means for heating comprises an electric heater wire secured to a surface of said deformed member.

7. The apparatus according to claim 6 wherein said one jaw has means for removably receiving said heat recoverable member.

8. The apparatus according to claim 7 wherein said one jaw has means for making electrical connection to said electric heater wire when said heat recoverable member is inserted in said jaw.

9. The apparatus according to claim 8 wherein said heat recoverable means includes means permitting partial insertion thereof in said one jaw whereby to drive less than all possible of said staples.

10. The apparatus according to claim 2 further comprising
means for selectively driving only some of said staples.

11. The apparatus according to claim 10 wherein said means for selectively driving includes means for causing said means for driving to contact only some of said staples.

12. The apparatus according to claim 2 wherein said means for heating includes an induction coil.

13. The apparatus according to claims 1 or 2 wherein one of said jaws carries at least one staple.

14. The apparatus according to claim 13 wherein said deformed member and said staple are separate parts.

15. The apparatus according to claim 13 wherein said deformed member and said staple are a unitary part.

16. The apparatus according to claim 15 wherein said at least one staple has one or more tines having a shape memory in an inwardly directed position relative to one another.

17. The device according to claim 13 wherein said means for heating comprises means for passing an electric current through said staple, said staple being in its deformed state with the tines thereof in the straightened position for passing through said material.

18. The apparatus according to claim 13 wherein said staple has four tines.

19. The stapling device of claim 13 wherein said means for heating heats said first means.

20. The apparatus according to claim 13 wherein said pair of elongated parallel jaws are annular in shape and coaxial.

21. The apparatus according to claim 20 wherein said means for driving is generally annular in shape about said coaxial axis.

* * * * *